United States Patent
Eriksson

(10) Patent No.: US 11,839,776 B2
(45) Date of Patent: Dec. 12, 2023

(54) SYSTEM AND METHOD FOR RADIATION TREATMENT PLANNING

(71) Applicant: RaySearch Laboratories AB, Stockholm (SE)

(72) Inventor: Kjell Eriksson, Bålsta (SE)

(73) Assignee: RaySearch Laboratories AB, Stockholm (SE)

(*) Notice: Subject to any disclaimer, the term of this patent is extended or adjusted under 35 U.S.C. 154(b) by 178 days.

(21) Appl. No.: 15/733,906

(22) PCT Filed: Jun. 25, 2019

(86) PCT No.: PCT/EP2019/066844
§ 371 (c)(1),
(2) Date: Dec. 1, 2020

(87) PCT Pub. No.: WO2020/002334
PCT Pub. Date: Jan. 2, 2020

(65) Prior Publication Data
US 2021/0220671 A1    Jul. 22, 2021

(30) Foreign Application Priority Data
Jun. 29, 2018  (EP) .................................. 18180987

(51) Int. Cl.
*A61N 5/10*    (2006.01)
(52) U.S. Cl.
CPC ......... *A61N 5/1037* (2013.01); *A61N 5/1031* (2013.01); *A61N 5/1038* (2013.01); *A61N 2005/1087* (2013.01)
(58) Field of Classification Search
CPC .. A61N 5/1031; A61N 5/1037; A61N 5/1038; A61N 2005/1087
See application file for complete search history.

(56) References Cited

U.S. PATENT DOCUMENTS

| | | | |
|---|---|---|---|
| 2008/0081991 A1* | 4/2008 | West | A61N 5/1031 600/407 |
| 2014/0275704 A1* | 9/2014 | Zhang | A61N 5/1067 600/1 |

(Continued)

FOREIGN PATENT DOCUMENTS

| | | | | |
|---|---|---|---|---|
| EP | 1 905 482 A1 | 4/2008 | | |
| EP | 2223720 A1 * | 9/2010 | ............. | A61N 5/103 |

(Continued)

OTHER PUBLICATIONS

Menten, Martin J., et al., "Lung stereotactic body radiotherapy with an MR-linac Quantifying the impact of the magnetic field and real-time tumor tracking," Radiotherapy and Oncology, 119(3): pp. 461-466, 2016.

*Primary Examiner* — Thaddeus B Cox
*Assistant Examiner* — Marc D. Honrath
(74) *Attorney, Agent, or Firm* — Faegre Drinker Biddle & Reath LLP

(57) ABSTRACT

A method of radiotherapy treatment planning involves dynamic target tracking and beam redirection. A set of 3D images of a patient reflecting a movement of the patient is obtained, and each image is deformably registered with one reference image. The accumulated dose is calculated as the sum of the dose distribution over all phases in dependence of the patient movement and the model of the delivery machine, the dose distribution for each phase being deformed by means of the deformation map for the respective phase, to match the reference image.

17 Claims, 2 Drawing Sheets

(56) References Cited

U.S. PATENT DOCUMENTS

| | | | |
|---|---|---|---|
| 2015/0265851 A1 | 9/2015 | Ma et al. | |
| 2017/0232274 A1* | 8/2017 | Isola | A61N 5/1045 600/1 |
| 2020/0261743 A1* | 8/2020 | Joe Anto | A61N 5/1037 |

FOREIGN PATENT DOCUMENTS

| | | |
|---|---|---|
| JP | 2014-042815 A | 3/2014 |
| WO | WO-2016/023786 A1 | 2/2016 |
| WO | WO-2017/109632 A1 | 6/2017 |
| WO | WO-2018/116354 A1 | 6/2018 |

* cited by examiner

SYSTEM AND METHOD FOR RADIATION TREATMENT PLANNING

This application is the National Stage of International Application No. PCT/EP2019/066844, filed Jun. 25, 2019, and claims benefit of European Patent Application No. 18180987.2, filed Jun. 29, 2018, the entire contents of which are incorporated by reference herein.

TECHNICAL FIELD

The present invention relates to a method, a computer program product and a computer system for radiation treatment planning, in particular for treatment planning using dynamic target tracking.

BACKGROUND

In radiation treatment, photons or charged particles are used to treat a patient. The radiation is used to treat tumorous cells but will also harm tissue surrounding the tumor. There is therefore a constant desire to improve radiation treatment planning and delivery to obtain the best possible effect on the target while causing minimal damage to surrounding tissue and in particular to organs at risk such as the spinal cord or the heart. The treatment is normally delivered in fractions, for example one fraction per day.

One problem in radiation treatment is that the patient's position and other setup parameters can change slightly between planning and delivery, and also between fractions. Also, the patient geometry may change during one fraction. In particular, when treating the torso, the patient's breathing cycle will often cause the target and other parts of the body to move in a cyclical way.

To account for the uncertainty in the target's position, a margin is often defined around the target to define a planning target volume, PTV, which is treated as the target for planning. This ensures a minimum dose to the whole target but also leads to unwanted radiation to surrounding tissue. Similarly, margins may be added around organs at risk to ensure that an organ at risk does not receive a too high dose even if its position is not precisely known. This may affect the possibility to ensure necessary dose to the target.

Robust planning is also used to account for uncertainties in the position of the target and/or organs at risk. In robust planning, a number of possible scenarios are considered, each scenario defining a modification with respect to the considered uncertainties, for example a shift in the patient setup or in the position of one or more targets and organs to account for organ motion during delivery. Several methods for robust planning may be applied including creating a plan that holds a certain minimum quality even for the worst possible scenario or creating a plan where the expectation value is considered. As is the case for planning treatment volumes, the tradeoff for reducing the uncertainties in tumor coverage is increased dose to healthy tissue. If the uncertainties can be reduced, the dose to healthy tissue can be reduced while maintaining the dose to the target.

Dynamic target tracking enables the beams to be redirected as the target moves with the intent to always hit the intended target volume, which means that the variations in the target's position are taken into account during the delivery of a treatment fraction, thus increasing the chance that the radiation hits the target, and avoids surrounding tissue, even as the target moves. In currently available dynamic tracking systems, the control system of the delivery system handles the actual tracking and makes sure that the intended volume is irradiated during the treatment. Therefore, dynamic target tracking allows the treatment margins around the target, or the geometrical shifts applied between the scenarios in robust planning, to be reduced and still ensures a sufficient dose to the target while sparing healthy tissue. Different methods may be used to track the target's movement during delivery, including MR or ultrasound, or applying a detectable marker to the target. The relative positions of the radiation source and the patient may be changed in a number of different ways. For example the radiation source may be moved by means of a robotic arm, or the couch holding the patient may be moved relative to the source. A lateral movement may also be achieved by moving the whole collimator opening. Alternatively, a gimbal may be used to redirect the beam to follow the target's movement. In proton treatment the beam may be redirected in a similar way by means of magnets. As is known in the art, several treatment techniques may be combined, which may require different ways of handling uncertainties. For example, if both photon and proton radiation are used tracking may be used for only one type of radiation, or two different tracking techniques may be used.

Medical Physics, 43 (5):2387-2398, May 2016: Electromagnetic guided couch and multileaf collimator tracking on a TrueBeam accelerator, describes the Varian TrueBeam® 2.0 accelerator, which includes a prototype tracking system with selectable couch or MLC compensation.

Radiotherapy and Oncology, 119(3):461-466, June 2016: Lung stereotactic body radiotherapy with an MR-linac Quantifying the impact of the magnetic field and real-time tumor tracking, describes the use Elekta's MR-linac for dynamic target tracking using MR as control signal.

In known target tracking methods, a treatment plan is obtained based on a planning image, as is common in the art. During delivery, the movement of the target is tracked in a suitable way and the control system ensures that the beam follows the target based on its tracked movement. Different methods of tracking the target movement includes MR, ultrasound or inserting a detectable marker in the target.

One problem with target tracking is that as the target moves within the patient, for example, because of breathing, other organs move as well, and their relative positions may change. This means that a beam that hits the target and avoids an organ at risk in one phase of the breathing cycle, may hit the organ at risk when the beam is moved to adapt to the target's position in another phase.

A key feature of planning for dynamic target tracking methods is to determine a good division of the dose over the whole cycle to ensure that the total dose is appropriate even if the breathing cycle is irregular.

Physics in Medicine and Biology, 62 (4):1480-1500, February 2017. Planning 4D intensity-modulated arc therapy for tumor tracking with a multileaf collimator, discloses a four-dimensional (4D) planning scheme of IMAT (i.e. VMAT) using 4D CT for planning tumor tracking with dynamic multileaf beam collimation. Each control point of the IMAT-delivery process is associated with an image set of 4D CT at a specified respiratory phase. First a normal (3D) IMAT plan is optimized on one of the phases. A 4D plan is then created by transforming the segments of the optimized 3D plan by using a 3D deformation method based on the target projections in the beam's eye view at different respiratory phases.

This method enables dose planning and monitoring, but has some severe limitations. The resulting plan relates to a fixed breathing pattern and there is no control of delivery in dependence of the actual breathing pattern. For the plan to function as intended, therefore, the patient's breathing pattern during delivery may not deviate neither in period nor in amplitude, from the breathing pattern during planning. The planning method also does not consider the possible movement of targets and organs at risk relative to each other.

SUMMARY

It is an object of the present invention to improve treatment planning plans using dynamic target tracking in radiotherapy treatment.

The invention relates to a method of radiotherapy treatment planning which allows for dynamic target tracking, more specifically, a method of radiotherapy treatment planning, involving dynamic tracking of a target for directing a beam in dependence of a change in patient geometry with time including a change in the position of the target with time, comprising the steps of a. obtaining a 4D image of a patient, comprising a set of 3D images, each 3D image corresponding to a phase in which the target has a specified position, the phases constituting a set of phases,
b. obtaining a model of the treatment machine, including machine limitations for the treatment machine,
c. obtaining an optimization problem comprising at least one dose-based optimization function defined on one or more total doses, based on a phase dose for each phase,
d. using the dose-based optimization function to optimize beam setups for dose delivery for each phase, by applying direct machine parameter optimization considering the machine limitations during optimization, wherein the phase dose for each phase is calculated based on a 3D image representing that phase and the beam setups representing that phase, and
e. obtaining one of more total doses from the calculated dose to each phase.

The total dose is preferably an accumulated dose calculated as a weighted sum of the dose calculated for each phase. Normally, a treatment plan is delivered to a patient in a number of fractions, for example, one fraction of the plan per day for a number of days. The total dose may refer to the total dose over the whole treatment plan for the patient, or the total dose for one fraction of a treatment, or the total dose for a subset of the fractions. In the simplest case, the step of obtaining one or more total doses comprises retrieving the phase doses from the dose engine when calculating the optimization function value.

According to the invention, not only the movement of the target itself, but also the deformed patient geometry, is considered. Although the variations in geometry are typically cyclical, such as a breathing cycle, the method is also applicable to other types of movement, such as linear or irregular movement. Since the dose of each phase is considered during optimization the dose to the target and the dose to the organs at risk will be optimized for the geometry of each phase. This will reduce the risk of for example increased dose to an organ at risk if the target moves in front of the organ at risk in the beam direction in some of the phases, which might happen if the plan is created on a single 3D image. The machine limitations may suitably be based on the model of movement.

Moreover, the use of the dose delivered in the entire treatment course is a prerequisite for the use of biological indices as optimization functions. This is advantageous because a biological index is directly related to the goals for the treatment, increasing the chance that the dose resulting from the planning will give achieve these goals. Accordingly, the at least one optimization function is preferably defined in the dose domain and/or as a biological index.

The delivery of a treatment beam is divided into one or more sub beams. These sub beams could be for example control points or segments for photon beams, or energy layers or spots for charged particle beams. It is preferable that the machine model obtained in step b also includes a model of the treatment delivery as a function of time, which means a model of the temporal distribution of the sub beams. The model of the treatment delivery as a function of time will be different for different treatment techniques and different machines.

In one preferred main embodiment, the at least one dose-based optimization function is arranged to optimize the total dose as an accumulated dose computed from the phase dose to each of at least two phases, further comprising the steps of registering each of the 3D images with a selected reference image to obtain a deformation map for each phase,
during optimization, deforming the dose distribution for each phase being by means of the deformation map for the respective phase, to match the reference image,
calculating the total dose as a weighted sum of the deformed dose distributions to all phases.

The reference image may be a planning image of the patient obtained earlier, or one of the 3D images in the 4D image, or another suitable image of the patient. Alternatively, it may be an atlas image of the relevant region. As mentioned above, treatment is normally delivered in a number of fractions. To enable this, the at least one optimization function may be based on the accumulated dose over all phases and all fractions.

In a second preferred main embodiment, at least one total dose comprises one or more total phase doses, each related to one of the phases, each total phase dose being calculated from the phase dose of that phase as if that phase is the only phase occurring during the treatment, i.e. as if there were no motion. The term treatment in this case could refer to one treatment fraction, a subset of fractions or the total treatment including all fractions. In this case, the optimization function may be comprised of constituent optimization functions, each constituent optimization function being assigned to one phase and arranged to optimize the total dose of that phase. In this case, the optimization function is suitably a weighted sum of the constituent optimization functions, each constituent function assigned to one phase and arranged to optimize the total dose of the phase it is assigned to. The optimization problem may be defined as a worst case optimization problem, where for example the optimization function is defined to prioritize improvements in one or more constituent optimization functions having unfavorable function values.

The method according to the invention is based on determining one or more total doses, where each total dose is computed from one or more phase doses in one operation. Therefore, an optimization problem of the same form as for planning without dynamic target tracking may be used. This is advantageous, because users are normally familiar with such optimization problems. There are no restrictions on how to distribute the dose between the phases, which increases the chance of finding the optimal total dose distribution. As is common in the art, an optimization problem comprises a number of optimization functions, which may be objective functions or constraints. Objective functions are formulated as goals to strive towards (for example, minimizing the dose to a risk organ) whereas constraints are specified limitations (for example, setting a value for the maximum dose to the risk organ).

In some embodiments the dose-based optimization function is additionally based on at least one function parameter related to the total dose. The at least one function parameter may be a specified dose level for a treatment function.

During dose delivery, the treatment machine may behave in a different way from the model of the treatment machine used in the optimization. Similarly, if a model of the change in patient geometry is used, the actual patient motion during delivery may differ from the model used in optimization. Therefore, the method is preferably combined with robust optimization. Optimization should be robust with respect to one or more of the following:

uncertainties in the model of the change in patient geometry as a function of time,
uncertainties in the dose tracking accuracy of the treatment machine,
uncertainties in patient setup, density or organ motion.

For robust optimization, the at least one dose-based optimization function may include at least one optimization function related to the total dose and at least one optimization function related to a scenario dose. The skilled person is aware of how to implement robust optimization based on, for example worst-case optimization or expectation value optimization.

In the simplest embodiments, the beam shape is kept constant through all phases. The beam shape may also be constant but shifted based on the model of the delivery system used to deliver the beam. In other embodiments the optimization problem is defined to allow the beam to have different beam shapes in different phases, and if applicable the beam shape may be constrained during optimization based on a model of the delivery system used to deliver the beam. In this case the method also enables, for example, the distance of leaf travel of the collimator leaves during dose delivery to be reduced because the beam shape may be adapted to what is most suitable in a particular phase.

The beam setup is defined as all parameters affecting the beam, for example including beam angles, intensity (i.e. monitor units MU or segment weights) and collimator leaf positions in the case of a photon machine with a multi-leaf collimator (MLC), or including beam angles and intensity (i.e. spot weights) in the case of a proton machine with pencil beam scanning. The beam setup will normally vary between the phases. Accordingly, the step of optimizing beam setups may comprise optimizing one beam setup for a reference phase and calculating a beam setup for at least one other phase based on the beam setup in the reference phase a difference in patient geometry between the other phase and the reference phase, and the model of the machine. The beam setup may be calculated in such a way that the beam shapes and intensities are identical between the phases. Alternatively, the beam shape and/or the intensity may be allowed to vary between the phases. In another embodiment, the beam shape and/or intensities in the different phases may be optimized simultaneously to obtain optimal beam shapes and/or intensities for each phase.

The difference in patient geometry will typically be related to a change in position of one or more targets and/or organs at risk. The optimization of the beam setup should be based on the machine model describing how the beam setup is changed in dependence of target movement when dynamic target tracking is used. The optimization problem is in this case preferably defined to constrain the difference in the beam shape and/or intensities between at least two of the phases. The target may be the target towards the dose should primarily be aimed or some other organ or tissue portion in the patient. The reference phase is preferably but not necessarily associated with the selected reference image, Since the total geometry of each phase is considered, and not just the target, the actual position of each organ for each phase will be known more precisely, which means that dose to organs at risk can be avoided in a better way. This should reduce the risk of exposing healthy tissue and in particular organs at risk to unnecessary radiation.

As for other planning methods, margins may be applied around the target and/or organs at risk, to handle uncertainties in their positions. The method according to the invention enables such margins to be reduced, by handling more precisely the positions of all critical organs, including the target (or targets) and any organs at risk.

The method according to the invention is suitable for treatment planning for a number of different delivery techniques, including but not limited to segmental multi-leaf collimator (SMLC), dynamic multi-leaf collimator (DMLC), three-dimensional conformal radiotherapy (3DCRT), Volumetric arc therapy (VMAT), and pencil beam scanning (PBS).

The optimization problem may also include a penalty on at least one factor that increases tracking uncertainties. For example, collimator angles may be selected to minimize the deviation between leaf movement and target movement. This will improve the tracking performance.

The machine limitations to consider are the ones that are relevant for treatment planning in the sense that they may affect the delivery of the treatment plan. By taking the machine limitations into consideration, it is ensured that the plan will be deliverable in view of the machine properties of the treatment system, and preferably that machine properties will not cause a delay in delivery. In some embodiments, therefore, a model of the change in patient geometry as a function of time is obtained and used during optimization to ensure that the plan is compatible with the properties of the delivery machine. The model of change in patient geometry as a function of time and the machine model may be used in a preprocessing step before optimization or a postprocessing step after optimization to verify that the machine limitations will not be violated during tracking.

Preferably, the model of change in patient geometry as a function of time is applied when considering at least one of the following:
accumulating dose over the phases
prioritizing the constituent functions
considering the machine limitations during the optimization To facilitate the consideration of machine limitations, the beam setup may be optimized using direct machine parameter optimization, considering the machine limitations during optimization, based on a model of the delivery system. As an alternative, at least one portion of the beam setup, such as the collimator angle, may be pre-calculated before performing the inventive method to reduce tracking uncertainties. It is also possible, based on the model of the machine and the model of the change in patient geometry, to perform calculations to determine in advance whether it is possible to redirect the beam between two adjacent phases.

The model of the change in the patient's geometry as a function of time is based on the amount of time that the patient is in each phase. The model of the change in patient geometry may be a discrete function of the motion, in which case each phase is associated to a particular time slot in the discrete model. The model of the change in patient geometry may alternatively be a continuous function of the motion, in which case each phase is associated with a time slot in the continuous model. As above, each phase is associated with one of the 3D images that constitute the 4D image.

The simplest motion model is to define equal time in each phase. A slightly more advanced model is to assign different times in the different phases. More advanced both discrete or continuous time models could be applied, based on for example measurements of the motion or population statistics of the motion. Optimizing optimization functions based on accumulated dose has the advantage of not restricting the dose to individual phases. Instead only the accumulated dose for the entire fraction (or several fractions) which is the ultimate endpoint is considered during optimization, giving the optimizer the freedom to redistributing the dose between the phases in an optimal way, which increases the possibilities to improve plan quality.

In the weighted sum of the dose distributions or in the weighted sum of the constituent functions, the weights may be determined in different ways. In the simplest case, the weighted sum is computed given equal weight to each phase. Alternatively, the weights in the weighted sum may be based on the probability of each phase to happen. In this case, a model of the probability of each phase happening is required as input to setting the weights. A third option is to let the weights in the weighted sum be based on the time spent in each phase based on the model of patient motion as a function of time.

The method according to the invention may also be combined with robust optimization planning, by using a robust optimization function as the at least one optimization function. This includes, but is not limited to, robust planning techniques in which plans are calculated for a number of different scenarios to ensure that the plan with the lowest quality is still sufficiently good with respect to minimum dose to the target and maximum dose to other tissue, or that the expectation value of the dose distribution is sufficiently good. Combining robust optimization and dynamic target tracking means that the shifts between the scenarios can be reduced and enables handling of uncertainties with respect to the time model, so called interplay effects, tracking delivery. Uncertainties that may be handled by robust planning include the following:

uncertainties in the model of the change in patient geometry as a function of time, uncertainties in the control system of the dose delivery system, in particular the dose tracking accuracy, and uncertainties in patient setup, density or organ movement.

The robust optimization of at least one uncertainty may be handled in any manner known in the art, including the following:

worst-case optimization expectation value optimization application of margins

The robust optimization function may also be based on the probability of the patient being in each phase and/or on a model of patient motion as a function of time.

The invention also relates to a computer program product for controlling a radiotherapy planning apparatus, preferably stored on a carrier such as a non-transitory storage means, said computer program product comprising computer readable code means which when run in a processor of a radiotherapy planning apparatus will cause the apparatus to perform the method according to the above.

The invention also relates to a computer program product for controlling the delivery of a radiation treatment plan, preferably stored on a carrier such as a non-transitory storage means, said computer program product comprising computer readable code means which when run in a processor of a radiotherapy delivery apparatus will cause the radiotherapy delivery apparatus to receive information regarding the tracking of at least one region in the patient over time and control the delivery of a plan obtained by any one of the preceding claims in dependence of the received information.

The invention also relates to a radiotherapy treatment planning apparatus comprising a processor and a program memory holding a computer program product according to the above, arranged to be run in the processor to control the radiation treatment planning apparatus.

DETAILED DESCRIPTION

The invention will be described in more detail in the following, by way of example and with reference to the appended drawings, in which FIGS. 1a, 1b and 1c illustrates three methods of dynamic target tracking.

DETAILED DESCRIPTION

The goal of radiation treatment planning generally is to maximize the probability of complication free tumor control. This could in principle be achieved using biological optimization functions, such as TCP and NTCP based optimization functions. The optimization functions are part of the optimization problem and may be expressed as objective functions or as constraints. The clinical goals are usually stated in the dose domain, and therefore physical optimization functions, such as min and max dose, max average dose, min and max DVH points, are more commonly used. As is well known in the art, optimization functions are designed to create plans that fulfil clinical goals, by means of objective functions and/or constraints.

When creating a plan without dynamic target tracking, i.e. on the nominal phase only, the optimization function is related only to the nominal dose distribution. If for example one clinical goal is a 70 Gy uniform dose to the entire target, the optimizer will strive to achieve a uniform dose of 70 Gy to the target for the geometry of the nominal phase if a 70 Gy uniform dose optimization function is applied during optimization. An example of an optimization function is a dose-based optimization function striving to obtain a specified uniform dose to the target volume. Such a function can be denoted $f(D_L, D)$ where $D_L$ is the specified dose level and D is the dose computed to the planning CT, which may be one of the phases in a 4DCT.

Figure 1A:
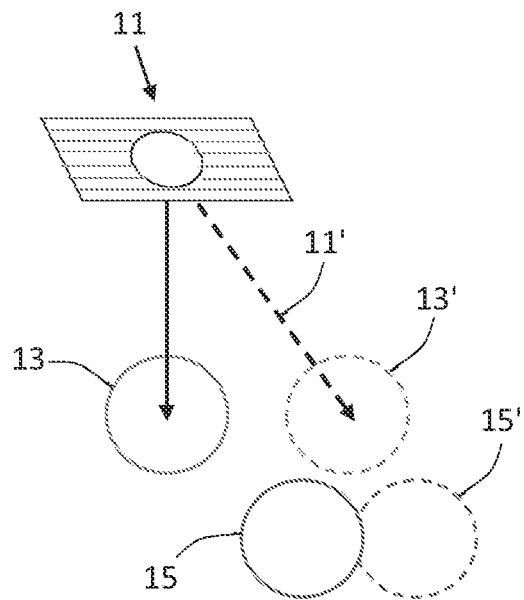
Figure 1B:
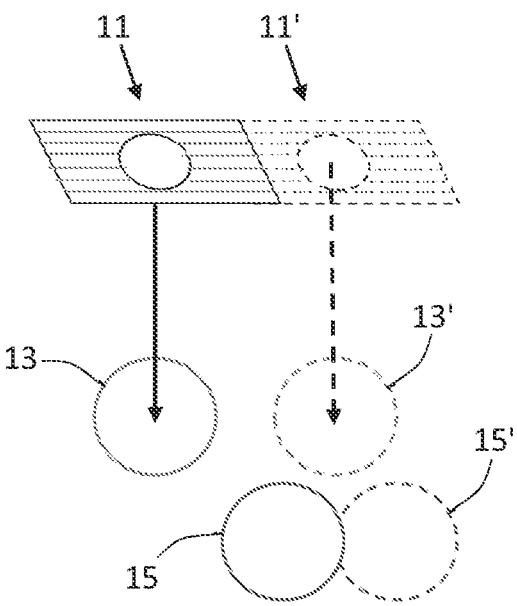
Figure 1C:
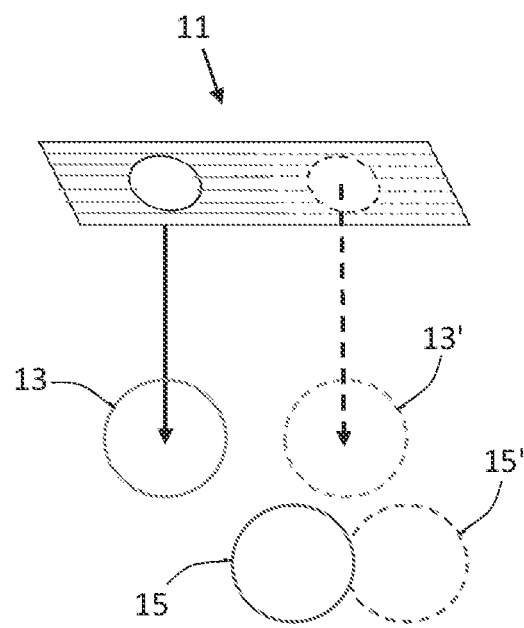

As mentioned above, techniques for dynamic target tracking have significantly improved treatment planning by enabling the beam to follow a moving target. FIGS. 1a, 1b and 1c illustrate three main methods known in the art for dynamic target tracking. Each of the FIGS. 1a, 1b and 1c shows, schematically, a beam source 11, a target 13 and an organ at risk 15 at a first position corresponding to a first phase indicated with solid lines. Treatment planning is based on the situation shown with solid lines in this example. The target 13' and the organ at risk 15' are also shown at a second point in time, corresponding to a second phase, using dashed lines. As can be seen, the relative positions between the target and the organ at risk changes between the first and the second point in time. This means that a beam that is designed to hit the target and avoid the organ at risk at the first point in time may not avoid the organ at risk at the second point in time. In dynamic target tracking, generally the movement is modelled and the time spent in each phase is approximated.

FIG. 1a illustrates gimbal tracking, in which the beam source 11 is kept in the same position but the beam angle is changed to follow the moving target 13. The first beam angle is shown as a solid line and the second beam angle is shown as a dashed line. As can be seen, the first beam will affect the target 13 in the first phase, but will avoid the organ at risk 15. In the second phase, the relative positions between the target 13' and the organ at risk 15' relative to the beam has changed so that in the beam 11' will affect the target 13' but also the organ at risk 15'. With gimbal tracking, since the beam angle changes there would be a risk of affecting the organ at risk even if the relative positions of the target and the organ at risk remained the same in a lateral movement.

A similar situation arises in proton therapy, when spot tracking is used. This involves changing the beam angle by means of magnets, which in the context of this invention is analogue to varying the beam angle with gimbal tracking.

FIG. 1b illustrates robotic tracking in which a robot arm is used to move the beam source 11 laterally to a new position 11' along with the target's 13 movement. Again, the beam at the first point in time is shown as a solid line and the beam at the second point in time is shown as a dashed line. As in FIG. 1a, the first beam will affect the target 13 but will avoid the organ at risk 15. In the second phase, the relative positions between the target 13' and the organ at risk 15' relative to the beam has changed so that in the beam will affect the target 13' but also the organ at risk 15'. An analogue situation results from couch tracking where, instead of a robot arm moving the beam source 11, the couch moves with the patient on it, to change the relative positions of the beam source 11 and the patient.

FIG. 1c illustrates MLC tracking. This is similar to robotic tracking but instead of moving the beam source, the opening in the collimator is moved laterally to a new position in the $2^{nd}$ phase, while maintaining the leaf positions, so that the beam will follow the movement of the target.

Figure 2:
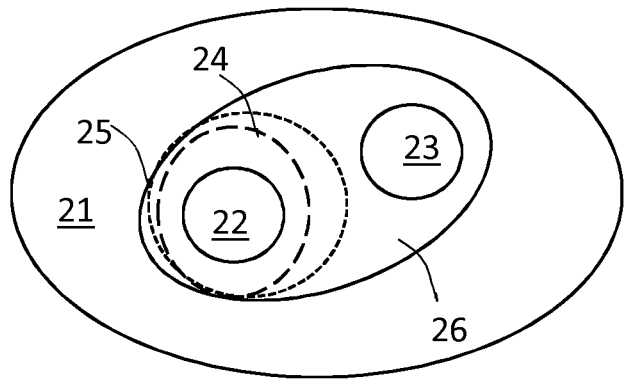
FIG. 2 illustrates the application of security margins around organs.

FIG. 2 illustrates different target volume definitions that may be used in robust planning. A simplified section through a patient 21 is shown, comprising a first 22 and a second target 23, typically tumors. The volume of each target identified as malignant growth is referred to as the gross tumor volume GTV. Around the first GTV 22 a clinical target volume CTV 24, delimited by a dashed line, is defined as the volume containing the GTV and/or a margin around it, typically including sub-clinical microscopic malignant disease. A planning target volume PTV delimited by a dotted line 25 may be defined around the CTV to allow for possible geometrical variations and/or movement of the patient. Similar CTV and PTV are not shown but may be defined for the second GTV 23. An internal target volume ITV 26 includes the two tumor volumes and any tissue between them. A treatment plan for irradiating both the first and the second target obtained with conventional methods has a high risk of unwanted dose to the healthy tissue between the targets, in the ITV. The CTV, PTV and ITV may be defined with regard to uncertainties in, for example, the treatment setup. There may also be one or more organs at risk, which may have their own margins to account for uncertainties, and that may also affect the margins applied to the CTV, PTV and ITV. The volume added by the CTV, PTV or ITV should be sufficient to ensure a satisfactory dose to each target but should also be kept to a minimum to avoid unnecessary radiation to surrounding tissue.

In general, the method according to the invention is based on an optimization problem comprising at least one optimization function defined on the entire treatment fraction dose or on the total dose over several fractions, preferably the entire treatment course, while considering the dose to the different phases within a treatment fraction. Such an optimization function can be denoted $$f(D_1, D_2, \ldots, D_m) \text{ or } f(a_1, a_2, \ldots, a_n, D_1, D_2, \ldots, D_m) \quad (1)$$

where $D_i$ is the dose computed on the 3D image of the i:th phase of the 4D image and at least one of the function parameters $a_j$ relates to the entire treatment fraction (or several treatment fractions). The parameter $a_j$ could for example be a dose level for a physical optimization function or the number of fractions in a biological optimization function.

The optimization function may, for example, be included in the optimization problem as a constituent function to the composite objective function or as a constraint function. An example of an optimization function is a dose-based optimization function striving to obtain a specified uniform dose to the target volume. Such a function can be denoted $$f(D_L, D_1, D_2, \ldots, D_m) \quad (2)$$

where $D_L$ is the specified dose level (the function parameter) for the entire treatment fraction (or several treatment fractions) and $D_i$ is the dose computed on the 3D image of the i:th phase of the 4D image.

An embodiment of the above method is based on defining a number of 3D images of the patient in different phases, and to use image registration between the phases to deform the dose of each phase to one reference image. The reference image may be, for example, the planning image, the nominal image or one of the phases. The total dose is then accumulated on the reference image using the deformation maps obtained by the registrations to deform the dose in each phase to match the geometry of the reference image. The optimization function of Eq. 2 then becomes $$f(D_L, D_1, D_2, \ldots, D_m) = f(D_L, D_{acc}(D_1, D_2, \ldots, D_m)), \quad (3)$$

where $D_{acc}$ is the accumulated dose computed from the dose of each phase, based on image registrations and a motion as a function of time.

Another embodiment of the above method is based on using constituent optimization functions defined on the dose of each phase, where these functions are combined in the optimization function. An example of an optimization function is a dose-based optimization function striving to obtain a specified uniform dose to the target volume. in this case, the function of Eq. 2 becomes $$f(D_L, D_1, D_2, \ldots, D_m) = f(g_1(D_L, D_1), g_2(D_L, D_2), \ldots, g_m(D_L, D_m)) \quad (4)$$

In this example all $g_i$ are identical constituent optimization functions striving to achieve the uniform dose $D_L$ in the i:th phase. The optimization f combines the function values of the constituent functions $g_i$. Examples of f are a sum of the constituent function values, a weighted sum based on, for example, the probability of a phase to occur or the time spent in each phase, or a minimax function that would strive to improve the constituent function of the phase with the worst function value or give higher priority to improve constituent functions with unfavorable function values.

An example of a more general function can be denoted as $$f(a_1,a_2,\ldots,a_n,D_1,D_2,\ldots,D_m)=f(a_1,a_2,\ldots,a_n,D_1, \\ D_2,\ldots,D_m,g_1(a_1,a_2,\ldots,a_n,D_1),g_2(a_1,a_2,\ldots, \\ a_n,D_2,)\ldots,g_{m-1}(a_1,a_2,\ldots,a_n,D_m),g_m(a_1, \\ a_2,\ldots,a_n,D_1,D_2,\ldots,D_m)),\quad(5)$$

with definitions as above. This definition would allow for example a combination of the two examples above using a combination of accumulated dose and constituent functions that depends on the dose of a single phase. Other definitions of $f(a_1, a_2, \ldots, a_n, D_1, D_2, \ldots, D_m)$ are possible, to include for example optimization functions on the expectation value of the fraction dose, voxel-wise worst case and objective wise worst case.

Using this strategy, the same uniform dose optimization function as in the general case can be used in the method according to the invention, applied to the accumulated total dose. In fact, all optimization functions traditionally used for non-DTT planning can be applied, including biological optimization functions since these models are dependent on the dose distribution. Biological optimization functions are therefore in this context considered to be dose-based optimization functions, even though the function value is a probability and no desired dose level is specified.

Figure 3:
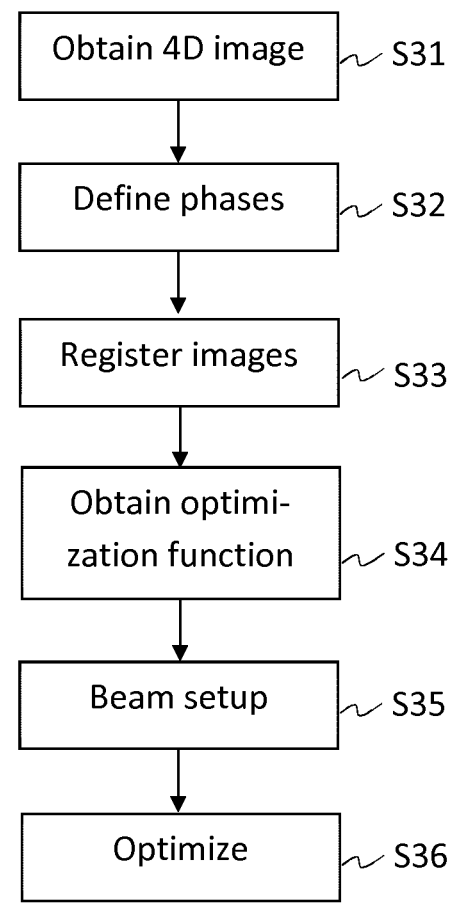
FIG. 3 is a flow chart of a method according to one embodiment of the inventive method.

FIG. 3 is a flow chart of a first embodiment of the method. It is assumed in this example that the beam shape remains the same in all phases and that the machine has an MLC. In this case the dose for all phases can be calculated based on one set of collimator leaf positions. In step S31 a 4D image of the patient is obtained. The 4D image is a set of 3D images over time, reflecting a movement cycle of the patient, for example a breathing cycle. The 4D image may be of any modality allowing dose calculations, including computed tomography (CT), cone-beam computed tomography (CBCT), proton CT (pCT), dual-energy CT (DECT) and Magnetic resonance (MR). The images describe the patient geometry in different phases, that is, as a function of time, for example by means of a time stamp per phase or measurements of the breathing cycle. Alternatively, synthetic 4D images may be created by measuring the motion of the target and applying deformable image registration. Instead of measuring the motion, population-based statistics could be used. Using a 4D image set, intermediate phases could be added using e.g. interpolation of the structures and deformable registration. The phases used could be a subset of the available phases in the 4D image. Although the best result will be achieved using images of the patient, a synthetic 4D image could also be used and might yield a satisfactory result.

In step S32 the cycle is divided into a set of phases, each corresponding to a patient geometry, and the phases are modelled as a function of time. In the simplest case, this means that it is determined how much time is spent in each phase. The whole set or a subset of the phases may be selected to be used in the optimization according to the following steps. By means of deformable registration, intermediate phases not included in the 4D image may be added.

To be able to use speed constraints and to be able to accumulate dose it is necessary to model the phases as a function of time. The simplest way would be to add a time stamp to each phase, i.e. to model how much time is spent in each phase, but any function that estimates the time in each phase may be used. Since the dose to the target is not necessarily the same in the different phases, the uncertainties in the time model could lead to differences between the optimized dose distribution and the actual delivered dose distribution. It is thus of importance to handle these uncertainties. Another reason for considering the uncertainties of the time model is that it could lead to violation of the speed constraints in the case where speed constraints are taken into account during optimization. This may be achieved by introducing a penalty in an objective function or a constraint related to the speed. Uncertainties may be handled in robust optimization or by setting a more restricting constraint than that prescribed by the model. How much more restricting the constraint should be depends on the magnitudes of the uncertainties.

In step S33 a reference image is selected and the images corresponding to the set, or subset, of phases are deformably registered to the reference image. The reference image may be one of the images in the 4D image, or a planning image, or any other image of the patient. It could also be a suitable atlas image of the relevant region. The registration allows the accumulation of doses delivered in all phases to be projected on the reference image to determine the total dose to each organ independently of the organ's movement during the treatment cycle.

In step S34 the dose-based optimization function is obtained for the accumulated dose over the whole cycle. The dose-based optimization function may be the same as for a method without dynamic target tracking, since the movement will be handled by the registration of each of the 3D images to the reference image.

In step S35 the beam setup is redirected for each phase. The beam setup includes settings for all variable machine parameters. The machine parameters differ with different delivery techniques, and may include gantry angle, MU, MLC leaf position, collimator angle, couch angle or gimbal angle, or in the case of pencil beam scanning spot weights. The skilled person is able to determine which machine parameter apply for each system. In the case where the same beam shape is used for all phases there is one common nominal beam shape. The MU is distributed over the phases based on the phase model defined in step S32 and in particular the time spent in each phase. As will be discussed below, it is also possible to allow the beam shape or MU to vary between the different phases.

The redirection is performed using the technique of the DTT delivery system. For example, if the delivery system uses robotic tracking or couch tracking, redirection will involve movement of the robotic head or couch shifts, respectively. If the delivery system uses gimbal tracking, the redirection will involve gimbal angle movement. For MLC tracking, the redirection will involve a shift of the entire leaf bank or the carriage (maintaining the beam shape of the MLC). The shift of the leaf bank can be done in the X and Y directions simultaneously. For pencil beam scanning, the or the scanning pattern and/or energy layers may be shifted. The applicable machine limitations on motion are considered when the redirection is performed before the optimization starts and/or during optimization.

In step S36 the beam setups are optimized using the optimization function defined in step S34. All beam setups are optimized simultaneously, using direct machine parameter optimization. In this way, the total dose can be distributed over the phases in the most suitable way.

In the embodiment where the beam shape is assumed to be constant, the optimization is preferably performed with respect to machine parameters for one of the phases. The dose for each of the other phases is then calculated during optimization by adapting machine parameters based on the movement of the target in all phases. The limits imposed by the properties of the delivery machine are included in the optimization function either as objective functions or as constraints, if applicable based on the model of the movement as a function of time.

As mentioned above, in other embodiments the beam shape may be adapted for each phase individually. The optimization will include optimizing one set of machine parameters for each phase in one optimization operation. The beam shape must be constrained in this case by a model of the dynamic target tracking control system, to avoid beam shapes that are unattainable or not feasible. A model of the control system of the DTT delivery system is used to constrain the beam shape and individual beam shapes per phase are optimized. This may be seen as a more general case of the method discussed above. When the beam shape is constant, the optimization variables are shared between the phases, while in the general case there may be one set of optimization variables per phase. The MU is distributed over the phases based on a model of the phases as a function of time, e.g. time spent in each phase.

In embodiments where the beam shape is allowed to change between phases, simultaneous direct machine parameter optimization of the beam setups of the optimized phases allows for individual beam shapes and/or MU in the different phases. The applicable machine constraints are taken into account during optimization to ensure that the plan is deliverable during target motion, that is, that the machine can adapt fast enough to the changing beam shapes during delivery. For robotic tracking this includes the speed of the robotic head, for gimbal tracking the pan and tilt angle speeds, for MLC tracking the leaf speed and possibly the jaw speed. For treatment couch it includes tracking the couch speed, and for PBS spot and energy layer switching time. Since each phase can be modelled as a function of time it is possible to use the actual speed constraints in the optimization function, as penalty functions or as hard constraints during optimization. Another option is to use a maximum allowed displacement in position or angle between two adjacent phases, if the time dependence is not known or too uncertain to model correctly. Different tracking techniques can be combined and accounted for during optimization. All degrees of freedom for the machine can be taken into account during optimization as for example collimator and couch rotations.

Yet another embodiment is applicable if it is possible to control the beam setup of each phase by means of the machine model, i.e. if it is possible to transfer information regarding the beam setup to be used in each phase to the DTT delivery system. In this case the beam setup may be optimized individually for each phase but can be predicted based on the machine model instead of being set by an operator. A model of the phases as a function of time, e.g. time spent in each phase, is used to constrain the motion of each phase. This could be achieved in two different ways. In the method according to the flow chart of FIG. 3, the machine model could be used to calculate the change in machine parameters for each respective phase. When implemented in the modified embodiment described above. The machine model can be used to define constraints on the movement between the different phases.

As a preparatory step before step S31, one or more parts of the beam setup may be calculated. These parts are selected so as to reduce tracking uncertainties, for example precalculating collimator angles that will minimize the deviation between the direction of leaf movement, and target movement. The leaf movement is determined based on the machine model and the target movement is determined based on the 4D images.

The dose-based optimization functions may be defined in different ways. At least one of the dose-based optimization functions may be defined as a biological index, including but not limited to tumor control probability (TCP) or Normal Tissue Complication Probability (NTCP). Alternatively, or in addition, at least one of the dose-based optimization functions may be defined in the dose domain, for example, in terms of uniform dose, minimum or maximum dos, minimum or maximum DVH, average dose, or gEUD.

The optimization function may also include a penalty on at least one factor that increases tracking uncertainties, such as collimator angles minimizing deviation between leaf movement and target movement. Alternatively, such parameters may be determined as preparation before performing the inventive planning method.

Figure 4:
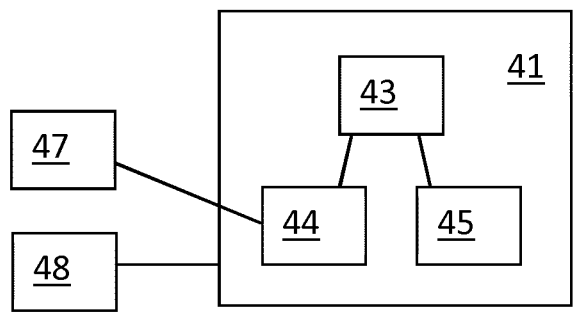
FIG. 4 shows schematically a computer system which may be used for treatment planning.

FIG. 4 is a schematic drawing of a computer system in which the method according to the invention may be performed. A computer 41 comprises a processor 43, a data memory 44 and a program memory 45. Preferably, one or more user input means 47, 48 are also present, in the form of a keyboard, a mouse, a joystick, voice recognition means or any other available user input means. The user input means may also be arranged to receive data from an external memory unit.

The data memory 44 comprises data to be used in the procedure, such as the precalculated plans and clinical goals. The program memory 45 holds a computer program arranged to make the computer perform the method steps discussed in connection with FIG. 3.

As will be understood, the data memory 44 and the program memory 45 are shown and discussed schematically. There may be several data memory units, each holding one or more different types of data, or one data memory holding all data in a suitably structured way, and the same holds for the program memories. For example, there may be separate memories or memory segments for precalculated plans, clinical goals and combined plans, respectively. One or more memories may also be stored on other computers.

The inventive method is suitably combined with robust optimization methods, for example regarding the following:
  uncertainties in the model for movement as a function of time
  uncertainties in the control system for the delivery system, that is, tracking-related uncertainties.
  other uncertainties, for example, regarding patient setup, organ movement, density, etc.
It will also be possible to minimize tracking uncertainties in other ways. For example, for collimator movement, aligning the MLC so that the leaf movement coincides with the direction of movement of the beam source will improve tracking performance.

When delivering the plan, the delivery apparatus is controlled by a computer program product arranged to deliver a plan obtained according to the invention, based on tracking information related to the movement of the tumor, received from a tracking system.

The invention claimed is:

1. A method of radiotherapy treatment planning, involving dynamic tracking of a target for delivery of a radiotherapy beam in dependence of a change in patient geometry with time including a change in position of the target with time, comprising the steps of:
  a. obtaining a 4D image of a patient, comprising a set of 3D images reflecting a movement of the patient, each 3D image corresponding to a phase in which the target has a specified position, the phase being one of a set of phases;

b. obtaining a model of a treatment machine, including machine limitations for the treatment machine;
c. obtaining an optimization problem comprising at least one dose-based optimization function defined on one or more total doses, based on a phase dose for each phase, wherein a total dose of the one or more total doses is a dose delivered to the patient over a whole treatment or over one or more fractions of the treatment;
d. using the at least one dose-based optimization function to simultaneously optimize all beam setups for dose delivery for each phase of the set of phases, by applying direct machine parameter optimization considering the machine limitations that are relevant to the radiotherapy treatment planning during the direct machine parameter optimization, wherein the phase dose for each phase is calculated based on a 3D image representing that phase and the beam setups representing that phase; and
e. obtaining one or more total doses from the phase doses that are calculated for the phases.

2. The method according to claim 1, wherein the at least one dose-based optimization function is arranged to optimize the one or more total doses as an accumulated dose computed from the phase doses to at least two phases, further comprising the steps of
f. registering each of the set of 3D images with a selected reference image to obtain a deformation map for each phase;
g. during the direct machine parameter optimization, deforming a dose distribution for each phase by means of the deformation map for the respective phase, to match the reference image; and
h. calculating the one or more total doses as a weighted sum of the deformed dose distributions to the at least two phases.

3. The method according to claim 2, wherein the reference image is one of the set of 3D images or a planning image of the patient.

4. The method according to claim 1, wherein the one or more total doses consist of one or more total phase doses, each related to one of the phases, each total phase dose being calculated from the phase dose of that phase as if that phase is the only phase occurring during the treatment.

5. The method according to claim 4, wherein the at least one dose-based optimization function comprises a number of constituent optimization functions, each constituent optimization function assigned to one phase and arranged to optimize the total dose of that phase.

6. The method according to claim 5, wherein the at least one dose-based optimization function is a weighted sum of the constituent optimization functions, each constituent function assigned to one phase and arranged to optimize the total dose of the phase it is assigned to.

7. The method according to claim 5, wherein the at least one dose-based optimization function is defined to prioritize improvement in one or more of the constituent optimization functions assigned to one or more phases having unfavorable function values.

8. The method according to claim 1, further comprising obtaining a model of the change in patient geometry as a function of time, corresponding to the phases and considering the model for at least one of the following:
accumulating dose over the phases;
prioritizing the constituent functions; or
considering the machine limitations during the direct machine parameter optimization.

9. The method according to claim 1, wherein the step of optimizing beam setups comprises optimizing one beam setup for each phase in such a way as to allow different beam shapes and/or intensities for different phases.

10. The method according to claim 9, wherein the optimization problem is defined to constrain a difference in the beam shapes and/or intensities between at least two of the phases.

11. The method according to claim 8, wherein the step of optimizing beam setups comprises optimizing a beam setup for a reference phase and calculating a beam setup for at least one other phase based on the beam setup of the reference phase, the difference in patient geometry between the other phase and the reference phase, the model of the treatment machine, and the model of the change in the patient geometry as the function of time.

12. The method according to claim 8, wherein the optimization problem is defined to account for uncertainties including one or more of the following:
uncertainties in the model of the change in patient geometry as a function of time;
uncertainties in a dose tracking accuracy of the treatment machine; or
uncertainties in patient setup, density or organ motion.

13. A computer program product for controlling a radiotherapy planning apparatus, stored on a non-transitory carrier, said computer program product comprising computer readable code means which when run in a processor of the radiotherapy planning apparatus will cause the apparatus to perform the method according to claim 1.

14. A computer program product for controlling delivery of a radiation treatment plan, stored on a non-transitory carrier, said computer program product comprising computer readable code means which when run in a processor of a radiotherapy delivery apparatus will cause the radiotherapy delivery apparatus to receive information regarding the tracking of at least one region in the patient over time and control the delivery of a plan obtained by claim 1 in dependence of the received information.

15. A radiotherapy treatment planning apparatus comprising the processor and a program memory holding the computer program product according to claim 13, arranged to be run in the processor to control the radiotherapy treatment planning apparatus.

16. A radiotherapy treatment planning apparatus comprising the processor and a program memory holding the computer program product according to claim 14, arranged to be run in the processor to control the radiotherapy treatment planning apparatus.

17. The method according to claim 1, wherein steps (a) through (e) are performed prior to the delivery of the radiotherapy beam by the treatment machine.

* * * * *